(12) United States Patent
Colvin, Jr. et al.

(10) Patent No.: US 7,800,078 B2
(45) Date of Patent: Sep. 21, 2010

(54) PRINTED CIRCUIT BOARD WITH INTEGRATED ANTENNA AND IMPLANTABLE SENSOR PROCESSING SYSTEM WITH INTEGRATED PRINTED CIRCUIT BOARD ANTENNA

(75) Inventors: Arthur E. Colvin, Jr., Mt. Airy, MD (US); John S. Gerig, Marco Island, FL (US); Paul Samuel Zerwekh, Shawsville, VA (US); Jeffrey C. Lesho, Brookville, MD (US); Benjamin N. McLeod, Reston, VA (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 1241 days.

(21) Appl. No.: 10/824,587

(22) Filed: Apr. 15, 2004

(65) Prior Publication Data

US 2004/0206916 A1  Oct. 21, 2004

Related U.S. Application Data

(60) Provisional application No. 60/462,695, filed on Apr. 15, 2003.

(51) Int. Cl.
*G01N 21/64* (2006.01)
(52) U.S. Cl. .................. 250/458.1; 250/484.4
(58) Field of Classification Search .............. 250/458.1, 250/484.4; 600/316, 317
See application file for complete search history.

(56) References Cited

U.S. PATENT DOCUMENTS

| | | | |
|---|---|---|---|
| 3,611,196 A | 10/1971 | Tornesch et al. | |
| 4,543,553 A | 9/1985 | Mandai et al. | |
| 5,001,054 A | 3/1991 | Wagner | |
| 5,003,622 A | 3/1991 | Ma et al. | |
| 5,117,825 A | 6/1992 | Grevious | |
| 5,126,714 A | 6/1992 | Johnson | |
| 5,244,810 A | 9/1993 | Gottlieb | |
| 5,300,911 A | 4/1994 | Walters | |
| 5,341,805 A | 8/1994 | Stavridi et al. | |
| 5,372,133 A | 12/1994 | Hogen Esch | |
| 5,517,313 A | 5/1996 | Colvin, Jr. | |

(Continued)

FOREIGN PATENT DOCUMENTS

EP   0 554 955 A1   8/1993

(Continued)

OTHER PUBLICATIONS

Kennedy, "Tailoring Polymers for Biological Uses," *Chemtech*, Feb. 1994, pp. 24-31.

(Continued)

*Primary Examiner*—David P Porta
*Assistant Examiner*—Marcus H Taningco
(74) *Attorney, Agent, or Firm*—Rothwell, Figg, Ernst & Manbeck, pc

(57) ABSTRACT

A printed circuit device used in conjunction with inductive power and data transmission applications is formed substantially of ferrite material, with an inductive coil conductor formed around the substrate to increase the electromagnetic properties of the coil for both power and data transmission functions, thereby eliminating the need for a discrete ferrite core wire-wound coil to be connected to the circuit device.

23 Claims, 7 Drawing Sheets

U.S. PATENT DOCUMENTS

| | | |
|---|---|---|
| 5,541,567 A | 7/1996 | Fogel et al. |
| 5,584,870 A | 12/1996 | Single et al. |
| 5,628,310 A | 5/1997 | Rao et al. |
| 5,704,352 A | 1/1998 | Tremblay et al. |
| 5,963,132 A | 10/1999 | Yoakum |
| 5,966,404 A | 10/1999 | Yokota et al. |
| 5,995,860 A | 11/1999 | Sun et al. |
| 6,002,954 A | 12/1999 | Van Antwerp et al. |
| 6,009,878 A | 1/2000 | Weijand et al. |
| 6,040,194 A | 3/2000 | Chick et al. |
| 6,073,050 A | 6/2000 | Griffith |
| 6,084,665 A | 7/2000 | Trainer |
| 6,092,530 A | 7/2000 | Weissman et al. |
| 6,099,482 A | 8/2000 | Brune et al. |
| 6,141,591 A | 10/2000 | Lenarz et al. |
| 6,143,432 A | 11/2000 | de Rochemont et al. |
| 6,183,304 B1 | 2/2001 | Hollander et al. |
| 6,198,950 B1 | 3/2001 | Kraus |
| 6,212,431 B1 | 4/2001 | Hahn et al. |
| 6,259,937 B1 | 7/2001 | Schulman et al. |
| 6,268,161 B1 | 7/2001 | Han et al. |
| 6,289,229 B1 | 9/2001 | Crowley |
| 6,321,067 B1 | 11/2001 | Suga et al. |
| 6,330,885 B1 | 12/2001 | Weissman et al. |
| 6,368,275 B1 | 4/2002 | Sliwa et al. |
| 6,376,824 B1 | 4/2002 | Michenfelder et al. |
| 6,387,048 B1 | 5/2002 | Schulman et al. |
| 6,400,338 B1 | 6/2002 | Mejia |
| 6,400,974 B1 | 6/2002 | Lesho |
| 6,402,689 B1 | 6/2002 | Scarantino et al. |
| 6,411,108 B1 | 6/2002 | Douglas et al. |
| 6,415,186 B1 | 7/2002 | Chim et al. |
| 6,419,624 B1 | 7/2002 | Burton et al. |
| 6,424,847 B1 | 7/2002 | Mastrototaro et al. |
| 6,430,444 B1 | 8/2002 | Borza |
| 6,443,891 B1 | 9/2002 | Grevious |
| 6,447,448 B1 | 9/2002 | Ishikawa et al. |
| 6,454,710 B1 | 9/2002 | Ballerstadt et al. |
| 6,475,750 B1 | 11/2002 | Han et al. |
| 6,505,059 B1 | 1/2003 | Kollias et al. |
| 6,542,777 B1 | 4/2003 | Griffith et al. |
| 6,545,483 B1 | 4/2003 | Douglas |
| 6,564,807 B1 | 5/2003 | Schulman et al. |
| 6,585,763 B1 | 7/2003 | Keilman et al. |
| 6,614,406 B2 | 9/2003 | Amundson et al. |
| 6,666,821 B2 | 12/2003 | Keimel |
| 6,671,527 B2 | 12/2003 | Petersson et al. |
| 6,682,490 B2 | 1/2004 | Roy et al. |
| 6,694,158 B2 | 2/2004 | Polak |
| 6,711,423 B2 | 3/2004 | Colvin, Jr. |
| 6,731,961 B2 | 5/2004 | Braig et al. |
| 6,731,976 B2 | 5/2004 | Penn et al. |
| 6,772,011 B2 | 8/2004 | Dolgin |
| 6,802,811 B1 | 10/2004 | Slepian |
| 6,806,552 B2 | 10/2004 | Woo et al. |
| 6,809,507 B2 | 10/2004 | Morgan et al. |
| 6,809,653 B1 | 10/2004 | Mann et al. |
| 6,809,701 B2 | 10/2004 | Amundson et al. |
| 2002/0016535 A1 | 2/2002 | Martin et al. |
| 2002/0019707 A1 | 2/2002 | Cohen et al. |
| 2002/0026108 A1 * | 2/2002 | Colvin, Jr. .................. 600/316 |
| 2002/0032435 A1 | 3/2002 | Levin |
| 2002/0118134 A1 | 8/2002 | Chen |
| 2002/0123779 A1 | 9/2002 | Zarinetchi et al. |
| 2002/0161288 A1 | 10/2002 | Shin et al. |
| 2003/0025645 A1 | 2/2003 | Amundson et al. |
| 2003/0030533 A1 | 2/2003 | Waffenschmidt |
| 2003/0050542 A1 | 3/2003 | Reihl et al. |
| 2003/0098783 A1 | 5/2003 | Pagnol |
| 2003/0113934 A1 | 6/2003 | Kwon |
| 2003/0125612 A1 | 7/2003 | Fox et al. |
| 2003/0140931 A1 | 7/2003 | Zeijlemaker et al. |
| 2003/0169169 A1 | 9/2003 | Wuidart et al. |
| 2003/0172940 A1 | 9/2003 | Rogers et al. |
| 2003/0181794 A1 * | 9/2003 | Rini et al. .................. 600/300 |
| 2003/0195400 A1 | 10/2003 | Glukhovsky |
| 2003/0213495 A1 | 11/2003 | Fujita et al. |
| 2004/0027306 A1 | 2/2004 | Amundson et al. |
| 2004/0048394 A1 | 3/2004 | Kirchhevel |
| 2004/0147801 A1 | 7/2004 | Kugler et al. |
| 2004/0181155 A1 | 9/2004 | Glukhovsky |
| 2004/0199059 A1 | 10/2004 | Brauker et al. |

FOREIGN PATENT DOCUMENTS

| | | |
|---|---|---|
| JP | 63-026109 | 2/1988 |
| JP | 08-166446 | 6/1996 |
| JP | 10-233469 | 9/1998 |
| JP | 11-108841 | 4/1999 |
| JP | 11-176998 | 7/1999 |
| TW | 466761 B | 12/2001 |
| TW | 476161 B | 2/2002 |
| WO | WO 00/13003 A1 | 3/2000 |
| WO | 0224048 A2 | 3/2002 |

OTHER PUBLICATIONS

IBM Technical Disclosure Bulletin "Simple Low Cost Inductor" vol. 38, No. 4, Apr. 1995 (3 pages).

* cited by examiner

PRINTED CIRCUIT BOARD WITH INTEGRATED ANTENNA AND IMPLANTABLE SENSOR PROCESSING SYSTEM WITH INTEGRATED PRINTED CIRCUIT BOARD ANTENNA

The present application claims the benefit of U.S. Provisional Patent Application No. 60/462,695, filed Apr. 15, 2003.

BACKGROUND OF THE INVENTION

1. Field of the Invention

This invention relates generally to electronic devices and methods for wireless data transmission and inductive powering of wireless data transmission devices. More particularly, the invention relates to implantable devices and methods for detecting and measuring certain characteristic parameters of a medium, such as, for example, the human body.

2. Background Art

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source. An analyte is allowed to permeate the fluorescent matrix, changing the fluorescent properties of the indicator material in proportion to the amount of analyte present. The fluorescent emission is then detected and measured by the photodetector, thus providing a measure of the amount or concentration of analyte present within the environment of interest.

One advantageous application of a sensor device of the type disclosed in the '313 patent is to implant the device in the body, either subcutaneously or intravenously or otherwise, to allow instantaneous measurements of analytes to be taken at any desired time. For example, it is desirable to measure the concentration of oxygen in the blood of patients under anesthesia, or of glucose in the blood of diabetic patients.

Because of the size and accessibility constraints on a sensor device implanted in the body, there are a number of issues associated with the production of a commercial unit, wherein the need for miniaturization gives rise to reliability, manufacturing cost-effectiveness, and performance concerns. For example, providing the sensing device with data transmission circuitry and/or a power supply would increase the required size of the device with respect to implantation in the body.

A processing system for processing the output signals of a sensor implanted in the body without the need for data transmission circuitry or an internal power supply is taught by U.S. Pat. No. 6,400,974, the disclosure of which also is incorporated herein by reference in its entirety. The '974 patent teaches a processing circuit that powers the sensor through inductively coupled RF energy emitted by the processing circuit. The processing circuit receives data transmissions from the implanted sensor as variations in the load on the processing circuit. The RF energy coupling and data transfer are accomplished by providing two coils: a small coil within the implanted sensor device, and a larger coil connected to the external processing circuit.

One possible implementation of the small coil would be to use a wire-wound coil having a discrete ferrite core attached to a printed circuit board (PCB). While such an implementation works acceptably, improvements can be made.

For example, the attachment of the discrete wire-wound ferrite core to the PCB may be difficult and give rise to reliability issues, resulting in low manufacturing yields.

Second, because each wire-wound coil from the manufacturer is slightly different in characteristics due to manufacturing tolerances, it may be necessary to individually tune each sensor device to properly match the frequency of operation with the associated antenna.

Additionally, the physical structure of the wire-wound coil creates a significant amount of void space within the volumetric displacement of the sensor device, which may result in bubble formation within the required polymeric encasement of the electronic circuit, resulting in a failed device.

A further issue is the requirement for axial alignment of the wire-wound coil ferrite core with the PCB. Alignment of the bent wire tether leads provided on the coil to be attached to the PCB may result in a radial size of the sensor package that is larger than necessary or desired for implantation applications.

Finally, the dimensions of a discrete wire-wound coil represent a limitation on the overall dimensions of the sensor device package; further size reduction of the device for implantation applications always being desirable.

In view of the foregoing, there remains a need in the art for an improved implantable sensor device.

SUMMARY OF THE INVENTION

In accordance with a first aspect of the present invention, a printed circuit device includes a substrate formed substantially of ferrite material, the substrate having main top and bottom surfaces, first and second side surfaces between the top and bottom surfaces along a major dimension thereof, and first and second end surfaces between the top and bottom surfaces along a minor dimension thereof, at least one component (either an integrated circuit (IC) chip, a discrete analog component, or an ASIC chip) mounted to a main surface of the substrate, and a conductor formed on the substrate and extending over at least one surface of the substrate in a coil pattern.

According to another aspect of the invention, a fluorescence sensor device includes a light source for introducing light into a fluorescent indicator that interacts with a medium, a photodetector for detecting light emitted by the fluorescent indicator in response to the introduced light, and for outputting a signal proportional to the detected light, the response of the fluorescent indicator varying in accordance with the presence and quantity of an analyte in the medium, a coil for receiving electrical power from an external power supply, and for communicating the signal to an external processing device; and a substrate formed substantially of ferrite material, the light source and the photodetector being mounted to a first section of the substrate, and the coil being formed on a second section of the substrate such that the coil extends around opposing surfaces of the substrate.

BRIEF DESCRIPTION OF THE DRAWINGS

The invention will be more fully understood with reference to the following detailed description of a preferred embodiment in conjunction with the accompanying drawings, which are given by way of illustration only and thus are not limitative of the present invention, and wherein.

DETAILED DESCRIPTION OF THE PREFERRED EMBODIMENT

Figure 1:
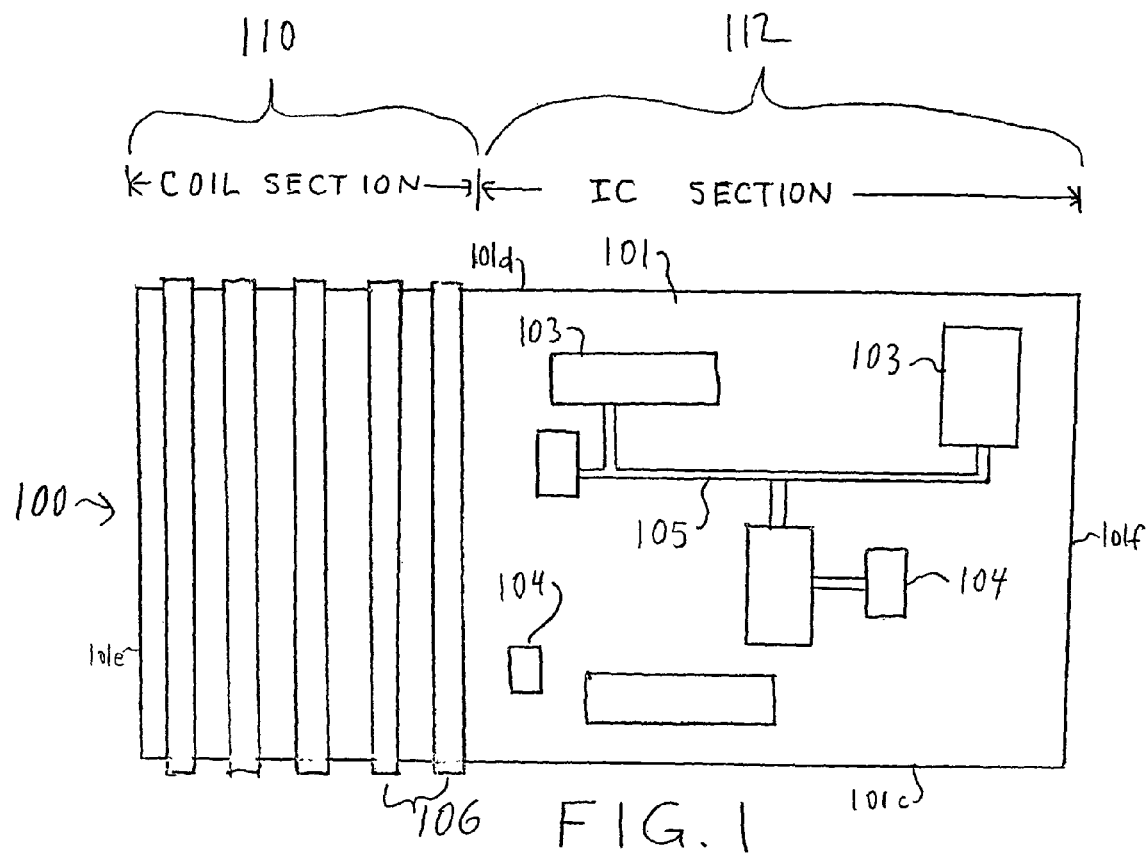
FIG. 1 is a top plan view of a sensor device circuit board according to one preferred embodiment of the invention.
Figure 2:
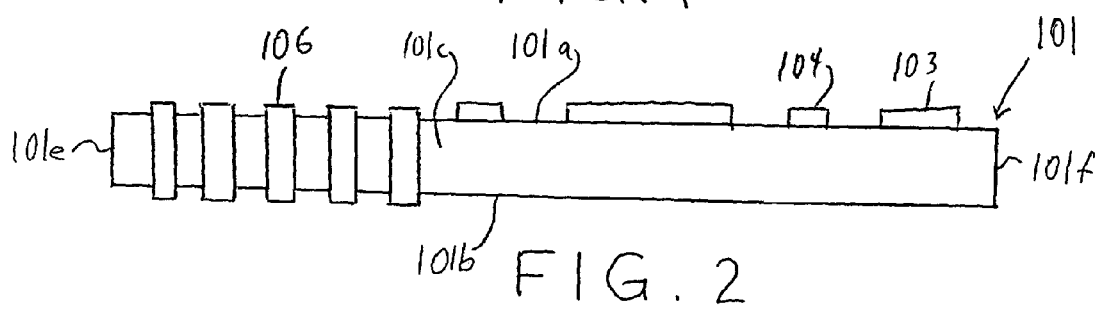
FIG. 2 is a side view of the sensor device circuit board of FIG. 1.
Figure 3:
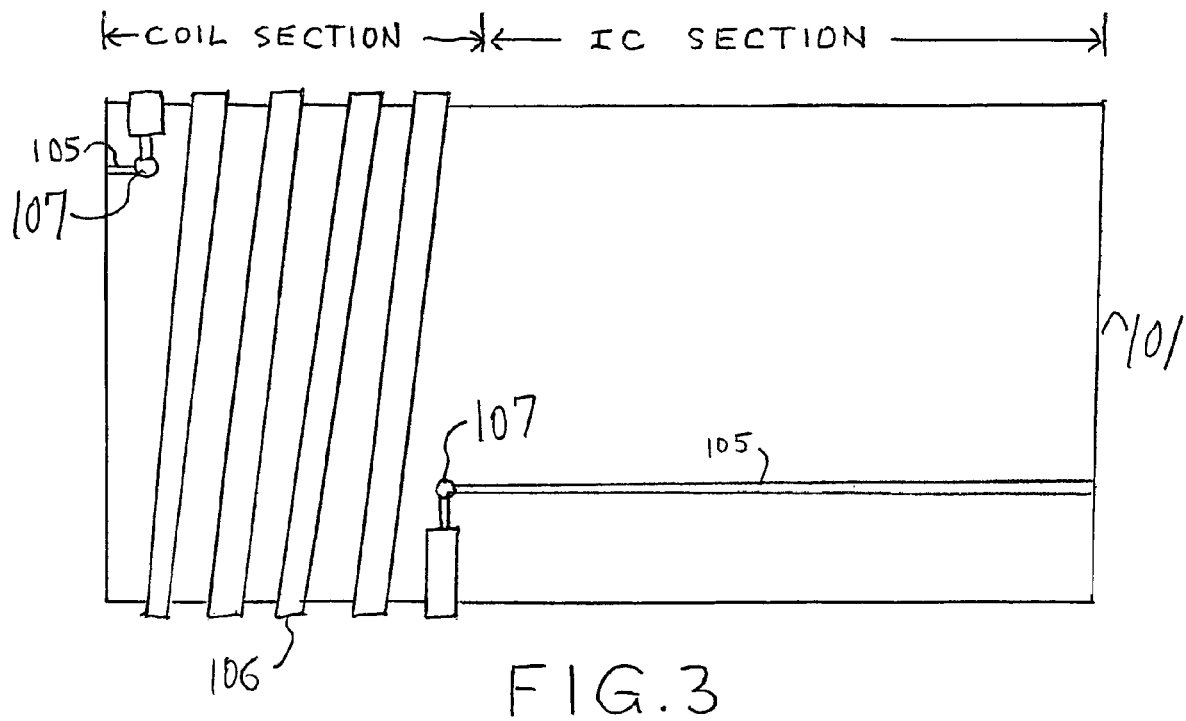
FIG. 3 is a bottom plan view of the sensor device circuit board of FIG. 1.

FIG. 1 shows a top view of one preferred embodiment of a sensor device circuit board according to the present invention. FIGS. 2 and 3 respectively show a side view and a bottom view of the sensor device circuit board.

According to a preferred embodiment of the invention, the sensor device circuit board 100 includes a substrate 101 made substantially of ferrite material. The substrate has main top and bottom surfaces 101a and 101b, end surfaces 101e and 101f extending along a minor dimension of the top and bottom surfaces, and side surfaces 101c and 101d extending along a major dimension of the top and bottom surfaces. The substrate preferably is organized into a coil section 110 and an integrated circuit (IC) section 112. The IC section 112 includes various circuit components 103, which may be IC chips, analog components, etc., and light-emitting diode (LED) chips 104 (different LEDs may be used for different measurements), interconnected by printed conductor wiring patterns 105 (an arbitrary pattern is shown in FIG. 1 for purposes of illustration).

While the circuit device of the present invention is described as a circuit "board" in connection with a preferred embodiment, it is not limited to any particular shape or configuration. In accordance with other embodiments, the ferrite circuit device may comprise at least one substantially flat surface on which the electronic components preferably are attached and curve-shaped side surfaces surrounding the top and bottom surfaces. For example, the ferrite circuit device may have a substantially flat surface that is substantially oval or round shaped. In another example, the ferrite circuit device may have a substantially flat top surface and curved bottom surfaces similar to, for example, one-half or ⅔ of a football. In yet other embodiments, the ferrite core may be rod-shaped. In still other embodiments, the ferrite core is shaped such that it has no substantially flat surfaces.

Also, while a preferred embodiment of the invention has been described as having a coil section on a first section of the substrate and the IC section being a second section of the substrate, the invention is not limited to this configuration. For example, in accordance with other embodiments, the circuit components may be mounted on top of the coil, resulting in thicker but shorter sensor. Further, the sensor illustrated in FIG. 6 could have a full length coil.

According to a preferred embodiment of the invention, the surfaces of the ferrite substrate to be metallized or otherwise applied with circuit components other than the side surfaces are pre-coated with a commercially available glazing compound which is fired at high temperature, to form an inert surface area for such metallization and/or component attachment. The surfaces of the substrate where the coil is to be applied all may be pre-coated with the glazing compound, or some may be pre-coated while others are not, or none of such surfaces may be pre-coated. One example of a preferred ferrite material formulation is Countis C-48; however, specialized ferrite formulations can be developed by those skilled in the art that are optimized for particular applications. As used herein, the term "substantially of ferrite material" encompasses any and all such formulations.

The thickness of the ferrite substrate for the implantable sensor application may be approximately 10 mils to approximately 250 mils, preferably approximately 20 mils to 100 mils and most preferably approximately 30 mils (0.030 inches) for miniaturization and power transmission considerations. If the ferrite core is substantially rod-shaped, or other curved surface, the diameter of the rod-shaped or curved surface may be approximately 10 mils to 250 mils, preferably 20 mils to 100 mils, most preferably approximately 30 mils. Again, other thicknesses may be used by those skilled in the art to optimize characteristics for other applications, and considerations such as size, frequencies and power levels.

The coil section 110 includes an elongated coil 106 which is preferably edge-wrapped around the ferrite substrate. The coil 106 is made of any suitable electrically conductive material, such as, for example, copper, gold, silver, or alloys. It is also possible for the coil 106 to be made of the same type of material as the printed wiring pattern 105. As shown in FIG. 3, the ends of the coil 106 may be directly connected to metallization contacts 107 formed on the ferrite substrate, which contacts connect to the printed circuit wiring patterns 105. The conductive coil material preferably is formed on the ferrite substrate 101 using edge-wrapping techniques. However, other formation techniques as known in the art also may be used. Also, while the coil is illustrated in FIG. 1 as being wrapped around the main surfaces and the side surfaces, the same effect may be obtained by having the coil pattern extending over only one of the main surfaces, or only around the side surfaces.

By making the entire printed circuit board from ferrite material, a single homogeneous substrate is provided, thus allowing the sensor device manufacturing process to be performed using standardized printed circuit manufacturing techniques. (Optionally, a thin layer of dielectric may be applied to the ferrite as a coating.) All manufacturing techniques available using a standard ceramic substrate also can be used with a ferrite substrate, including thick- and thin-film printed resistors and capacitors, wire bonding, surface mount technology (SMT), flip-chipping, and chip-on-board.

Additionally, the wire attach operation utilized in the ferrite core wire-wound coil may be eliminated. For example, the wrapped coil conductor 106 may be connected to the remainder of the circuit using standard metallization continuous surface routing techniques. The ability of such techniques to be automated provides a high degree of reproducibility and homogeneity in physical characteristics, as well as reliability, which is important for implant applications, and increases cost-effectiveness in manufacturing.

Further, by forming the entire printed circuit board of ferrite material, the length of ferrite may be increased substantially over the discrete ferrite core wound coil. For example, the length of the ferrite may be increased five-fold over the discrete ferrite core wound coil. This permits a significant increase in power transfer efficiency of electrical power from the external processing unit (not shown, see '974 patent) as compared with the discrete ferrite core wire-wound coil.

Figure 9:
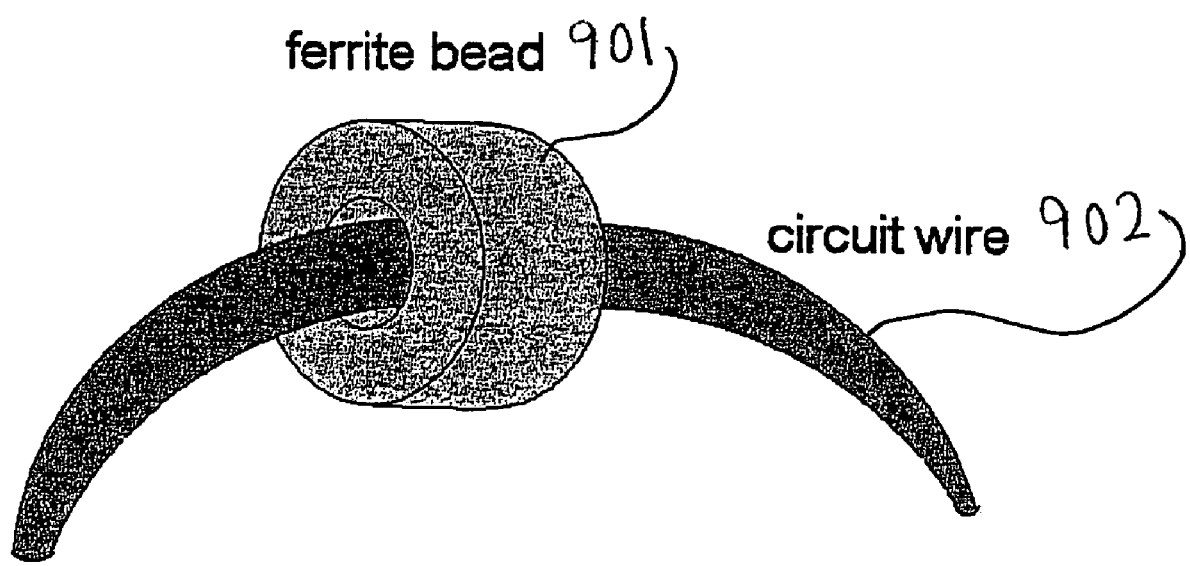
FIG. 9 is a schematic view of a ferrite bead used as a low-pass filter as another aspect of the invention.

An additional advantage provided by use of the ferrite substrate is noise suppression. Routing conductors through holes or vias formed in the ferrite substrate will act to damp high-frequency energy in the same manner as shown in FIG. 9, wherein a ferrite bead 901 is used as a low-pass filter around a circuit wire 902. Passing the circuit wire through the ferrite bead causes dampening of high-frequency components of current passing through the wire 902. Conversely, where such dampening is undesired, it is important that the coil be kept external to the ferrite substrate.

Figure 6:
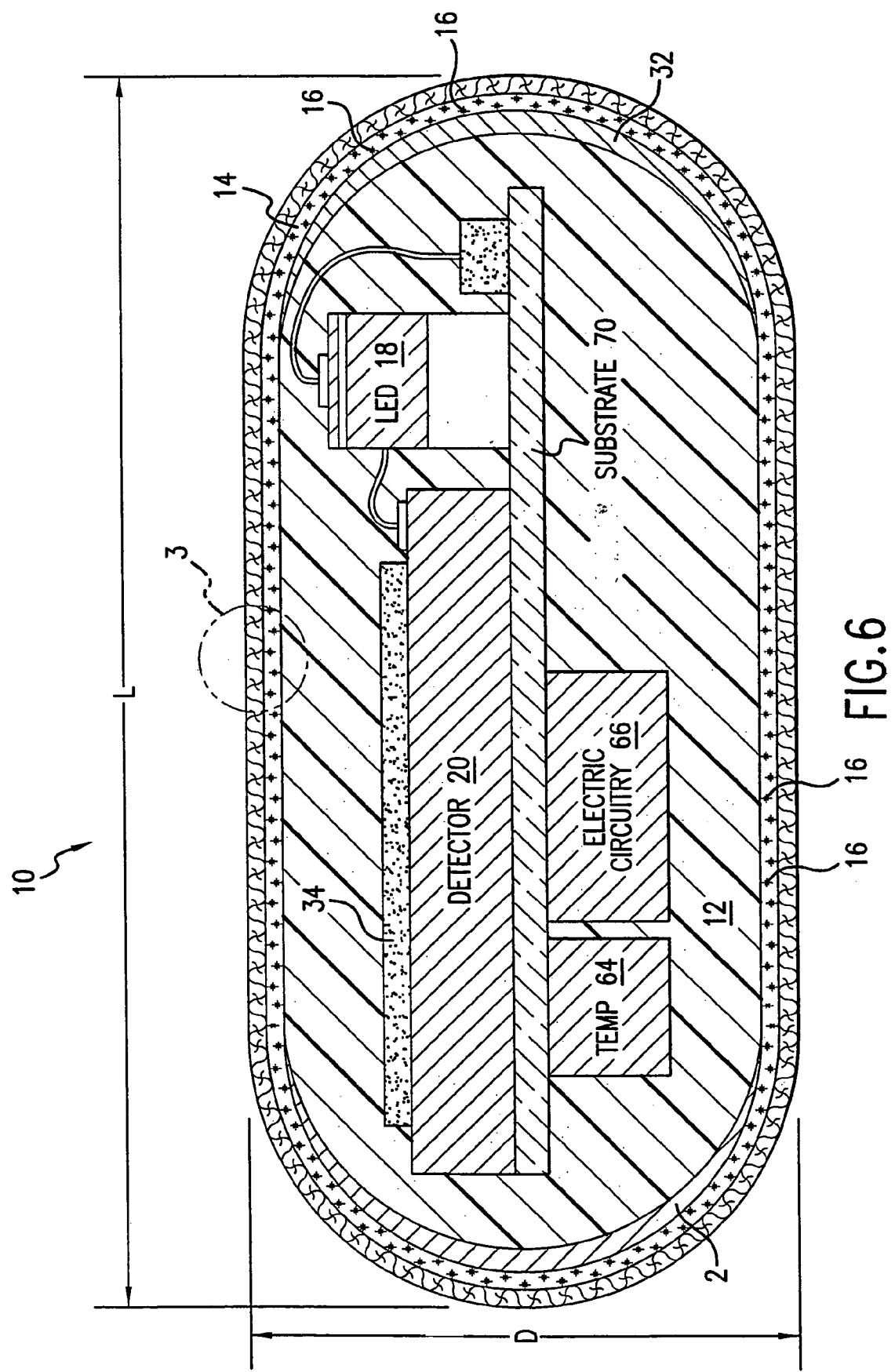
FIG. 6 is a schematic, section view of an implantable fluorescence-based sensor according to the invention.

Advantageous use of a ferrite material substrate to mitigate the effect of noise on other circuit components is illustrated by referring to an embodiment of a sensor 10 which operates based on the fluorescence of fluorescent indicator molecules, as shown in FIG. 6. The sensor 10 is composed of a sensor body 12; a matrix layer 14 coated over the exterior surface of the sensor body 12, with fluorescent indicator molecules 16 distributed throughout the matrix layer; a radiation source 18, e.g. an LED, that emits radiation, including radiation over a wavelength or range of wavelengths which interact with the indicator molecules, i.e., in the case of a fluorescence-based sensor, a wavelength or range of wavelengths which cause the indicator molecules 16 to fluoresce; and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules. The sensor 10 further includes a module or housing 66 containing electronic circuitry, and a temperature sensor 64 for providing a temperature reading.

To maximize the accuracy of the reading from the detector 20, the effect of ambient light incident on the detecting surface of detector 20 should be minimized. One method of accomplishing this is to drive the LED with a high frequency excitation signal, such that the effects of ambient light on detector 20 may be cancelled out. However, the high-frequency signal used to drive the LED may add undesirable on-board noise, which when present must be taken into consideration in designing the remainder of the circuit.

Undesirable on-board electrical noise can come from other sources as well. The sensor 10, having a coil 106 which is excited by a strong high-frequency magnetic field, may be surrounded and permeated by the high-frequency magnetic field. This high-frequency signal may add undesirable on-board electrical noise in various parts of the circuit, such as for example, in the LED 18 of sensor 10, which may adversely affect the operation of the overall device.

Figure 4:
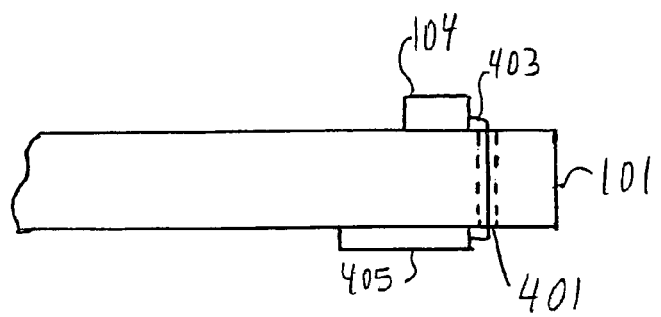
FIG. 4 is a partial side view of a sensor device circuit board according to a further embodiment of the invention.

By virtue of the ferrite substrate used as the PCB according to the invention, the deleterious effect of the high-frequency noise on other circuit components may be substantially mitigated by, for example, routing a drive lead wire through the ferrite substrate as a "via." As shown in FIG. 4, according to this aspect of the invention, a via 401 is formed through the ferrite substrate 111. LED 104 is mounted on one side of the substrate 101, and drive circuitry 405 can be mounted on an opposite side of the substrate 101. A drive signal conductor 403 from the drive circuitry 405 is routed to the LED 104 through the via 401, thus decreasing the effect of high-frequency noise into the LED drive. The ferrite substrate may be constructed having more than one via as needed to filter the noise. The lead wire from a circuit component may be routed through one or more vias as needed to filter noise. The lead wires from more than one circuit component may be routed through the same via or vias, or different vias.

Figure 5:
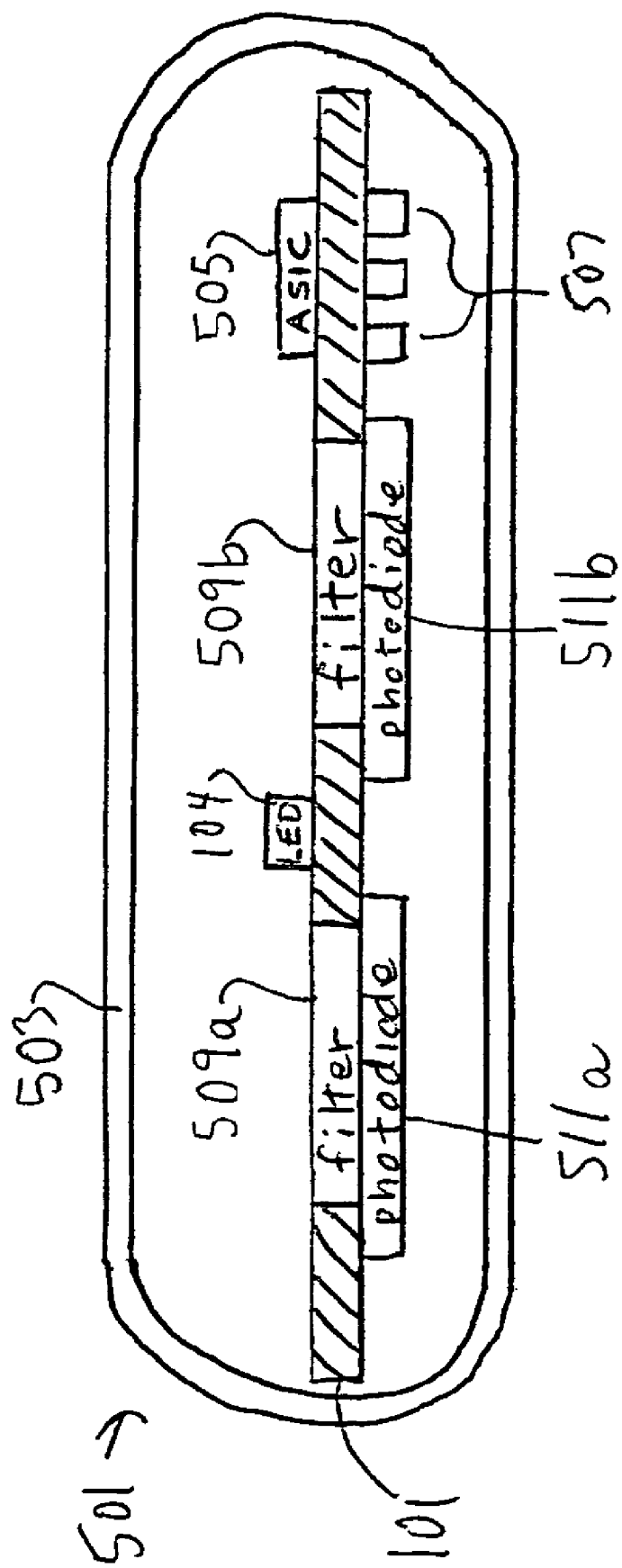
FIG. 5 is a cross-sectional view of a sensor device incorporating a sensor device circuit board according to a further embodiment of the invention.

According to another aspect of the invention, the undesirable effects of ambient light impinging on the photodetector are reduced, and the field of view of the photodetectors is increased, by moving the photodetector to the bottom surface of the ferrite substrate, opposite the surface on which the LED is mounted. This is shown in FIG. 5.

Figure 7:
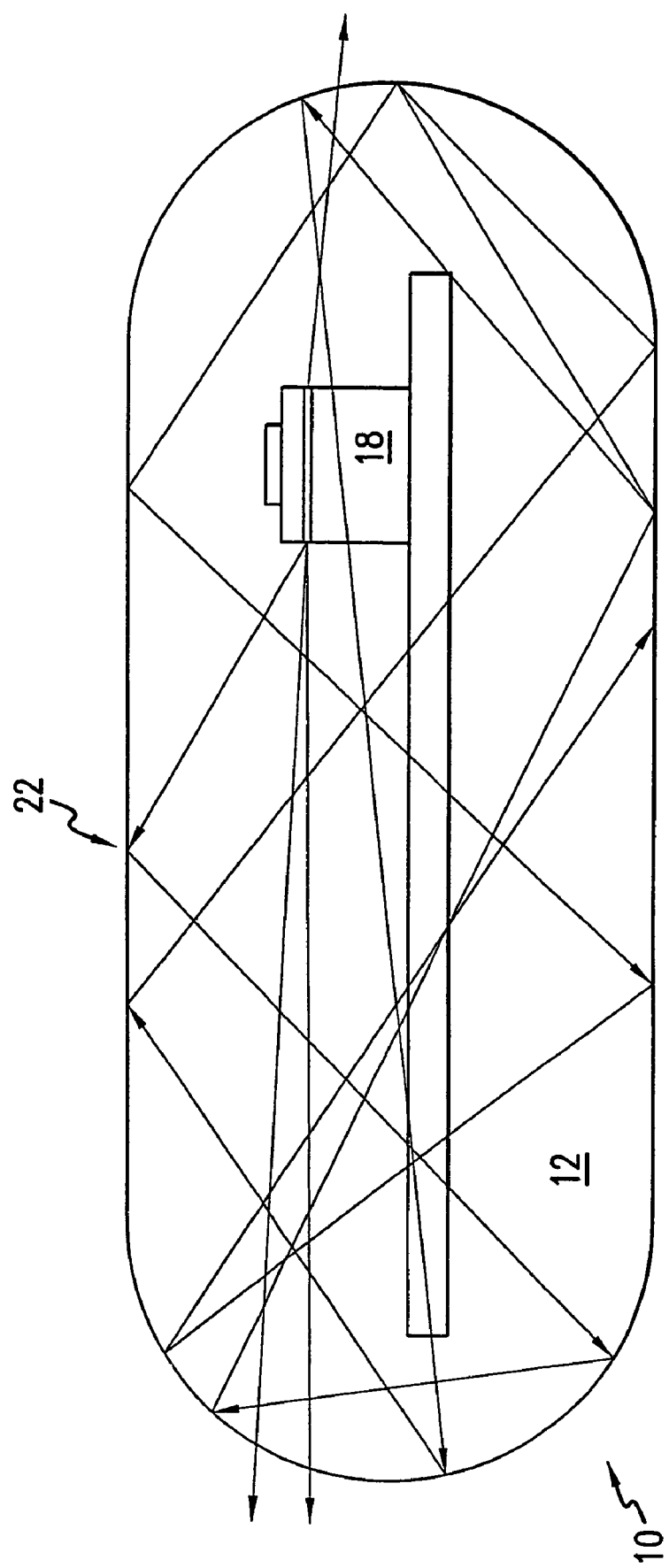
FIG. 7 is a schematic diagram of the fluorescence-based sensor shown in FIG. 6 illustrating the wave guide properties of the sensor.

By way of explanation, as shown in FIG. 7, radiation (e.g., light) is emitted by the radiation source 18 and at least some of this radiation is reflected internally at the surface of the sensor body 12, e.g., as at location 22, thereby "bouncing" back-and-forth throughout the interior of the sensor body 12.

It has been found that light reflected from the interface of the sensor body and the surrounding medium is capable of interacting with indicator molecules coated on the surface (whether coated directly thereon or contained within a matrix), e.g., exciting fluorescence in fluorescent indicator molecules coated on the surface. In addition, light which strikes the interface at angles (measured relative to a direction normal to the interface) too small to be reflected passes through the interface and also excites fluorescence in fluorescent indicator molecules. Other modes of interaction between the light (or other radiation) and the interface and the indicator molecules have also been found to be useful depending on the construction of and application for the sensor. Such other modes include evanescent excitation and surface plasmon resonance type excitation.

Figure 8:
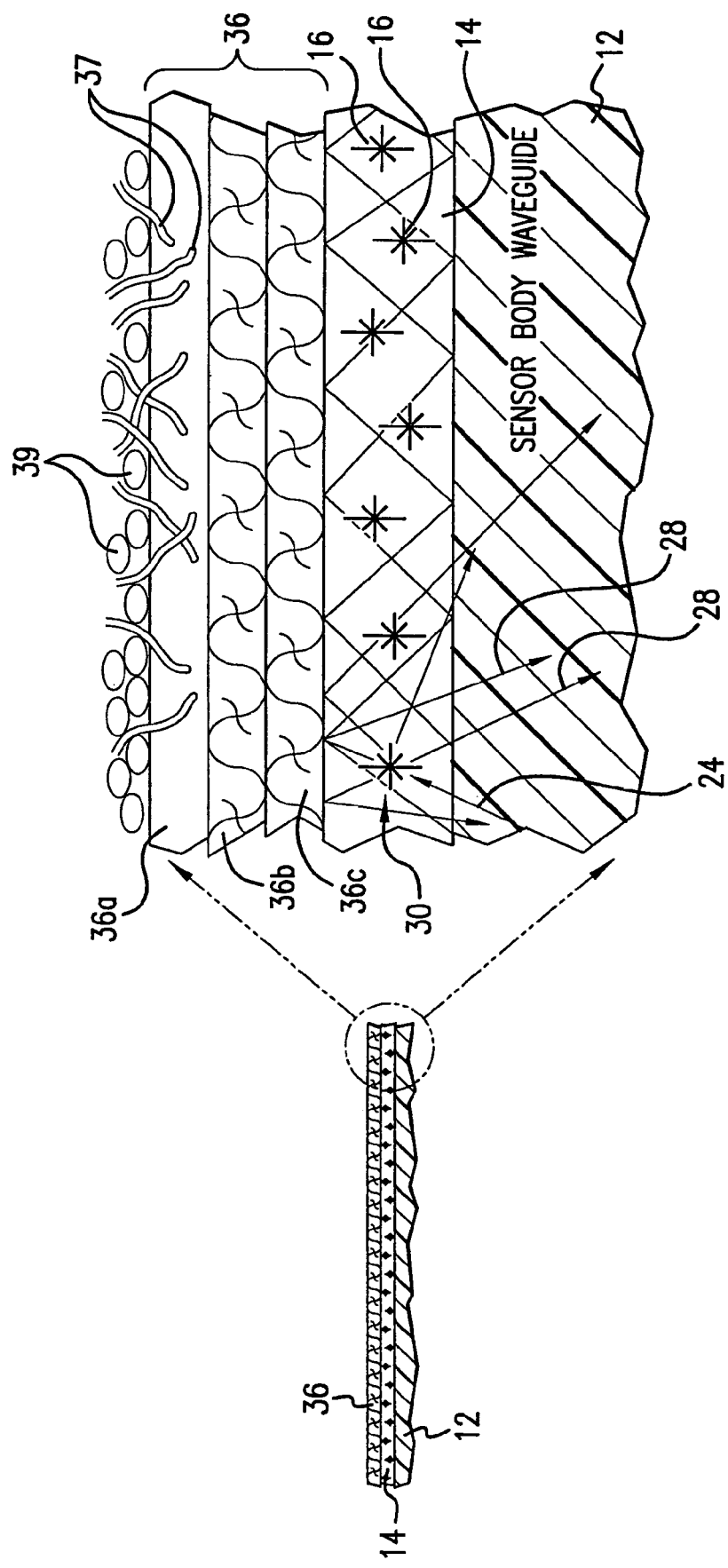
FIG. 8 is a detailed view of the circled portion of FIG. 6 demonstrating internal reflection within the body of the sensor and a preferred construction of the sensor/tissue interface layer.

As illustrated by FIG. 8, at least some of the light emitted by the fluorescent indicator molecules 16 enters the sensor body 12, either directly or after being reflected by the outermost surface (with respect to the sensor body 12) of the matrix layer 14, as illustrated in region 30. Such fluorescent light 28 is then propagated internally throughout the sensor body 12, much like the radiation emitted by the radiation source 18 is, and, like the radiation emitted by the radiation source, some will strike the interface between the sensor body and the surrounding medium at angles too small to be reflected and will pass back out of the sensor body.

In the prior sensor embodiment as shown in FIG. 6, an optical filter 34 preferably is provided on the light-sensitive surface of the photodetector 20, which is manufactured of a photosensitive material. Filter 34, as is known from the prior art, prevents or substantially reduces the amount of radiation generated by the source 18 from impinging on the photosensitive surface of the photosensitive element 20. At the same time, the filter allows fluorescent light emitted by fluorescent indicator molecules to pass through it to strike the photosensitive region of the detector. This significantly reduces noise in the photodetector signal that is attributable to incident radiation from the source 18.

Use of a ferrite substrate instead of the conventional white ceramic substrate provides a significant additional advantage in that the black ferrite material absorbs more incident light and thus scatters less incident light than the conventional white ceramic circuit board substrate.

As shown in FIG. 5, a sensor device 501 contains a ferrite PCB 101 and associated circuit components encased within sensor body 503. An optional ASIC controller 505 and associated other components 507, such as ICs, are mounted on the ferrite substrate along with an LED 104 and photodiodes 511a and 511b. In operation, photodiode 511a is used to measure the emitted fluorescence signal, while photodiode 511b is used to measure a reference signal. In an alternative embodiment, the photodiode 511b is used to measure a separate indicator signal at a different wavelength or with different indicators physically placed, for example, to measure 2 different analytes in the same sensor. First and second optical epoxy filters 509a and 509b are formed in the ferrite substrate by boring holes in the substrate and filling them with the epoxy filter material. Alternately, precision-fabricated glass filters may be glued into the holes.

By mounting the photodiodes 511a and 511b to the lower surface of the ferrite substrate directly under the optical filters 509a and 509b, the photodiodes are less susceptible to scattered LED and ambient light from sources other than the fluorescing indicator matrix; concomitantly, the upper surface of the ferrite substrate does not reflect any significant amount of light incident thereon, as contrasted with the conventional white ceramic circuit board substrate. Additionally, by relocating the photodetectors from the upper to the lower surface of the PCB substrate, larger angles of light from the indicator matrix are capable of impinging on the photodetector surfaces. Thus, more signal light is capable of being used to develop the photodetector signals, thereby further increasing the accuracy of the quantitative measurements. This configuration further enhances miniaturization by allowing the optical filters to be placed within the substrate and thus occupy no more space than the thickness of the substrate.

The sensor body 503 advantageously is formed from a suitable, optically transmissive polymer material (organic or inorganic) which will act as an optical wave guide. Preferred materials are acrylic polymers such as polymethylmethacrylate, polyhydroxypropylmethacrylate and the like, and polycarbonates such as those sold under the trademark Lexan®. The material allows radiation generated by the radiation source 104 (e.g., light at an appropriate wavelength in embodiments in which the radiation source is an LED) and, in the case of a fluorescence-based embodiment, fluorescent light emitted by the indicator molecules, to travel through it.

As further illustrated in FIG. 6, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator molecules. The reflective coatings may be formed, for example, from paint or from a metallized material.

The application for which the sensor 10 according to one aspect of the invention was developed in particular—although by no means the only application for which it is suitable—is measuring various biological analytes in the human body, e.g., glucose, oxygen, toxins, pharmaceuticals or other drugs, biomolecules, hormones, and other metabolic analytes. The specific composition of the matrix layer 14 and the indicator molecules 16 may vary depending on the particular analyte the sensor is to be used to detect and/or where the sensor is to be used to detect the analyte (i.e., in the blood or in subcutaneous tissues). Two preferred characteristics, however, are that the matrix layer 14 facilitate exposure of the indicator molecules to the analyte and that the optical characteristics of the indicator molecules (e.g., the level of fluorescence of fluorescent indicator molecules) are a function of the concentration of the specific analyte to which the indicator molecules are exposed.

To facilitate use in-situ in the human body, the sensor 10 is formed, preferably, in a smooth, oblong or rounded shape. Advantageously, it has the approximate size and shape of a bean or a pharmaceutical gelatin capsule, i.e., it is on the order of approximately 300-500 microns to approximately 0.5 inch in length L and on the order of approximately 300 microns to approximately 0.3 inch in depth D, with generally smooth, rounded surfaces throughout. The device of course could be larger or smaller depending on the materials used and upon the intended uses of the device. This configuration permits the sensor 10 to be implanted into the human body, i.e., dermally or into underlying tissues (including into organs or blood vessels) without the sensor interfering with essential bodily functions or causing excessive pain or discomfort.

Moreover, it will be appreciated that any implant placed within the human (or any other animal's) body—even an implant that is comprised of "biocompatible" materials—will cause, to some extent, a "foreign body response" within the organism into which the implant is inserted, simply by virtue of the fact that the implant presents a stimulus. In the case of a sensor 10 that is implanted within the human body, the "foreign body response" is most often fibrotic encapsulation, i.e., the formation of scar tissue. Glucose—a primary analyte which sensors according to the invention are expected to be used to detect—may have its rate of diffusion or transport hindered by such fibrotic encapsulation. Even molecular oxygen ($O_2$), which is very small, may have its rate of diffusion or transport hindered by such fibrotic encapsulation as well. This is simply because the cells forming the fibrotic encapsulation (scar tissue) can be quite dense in nature or have metabolic characteristics different from that of normal tissue.

To overcome this potential hindrance to or delay in exposing the indicator molecules to biological analytes, two primary approaches are contemplated. According to one approach, which is perhaps the simplest approach, a sensor/tissue interface layer—overlying the surface of the sensor body 12 and/or the indicator molecules themselves when the indicator molecules are immobilized directly on the surface of the sensor body, or overlying the surface of the matrix layer 14 when the indicator molecules are contained therein—is prepared from a material which causes little or acceptable levels of fibrotic encapsulation to form. Two examples of such materials described in the literature as having this characteristic are Preclude™ Periocardial Membrane, available from W.L. Gore, and polyisobutylene covalently combined with hydrophiles as described in Kennedy, "Tailoring Polymers for Biological Uses," Chemtech, February 1994, pp.24-31.

Alternatively, a sensor/tissue interface layer that is composed of several layers of specialized biocompatible materials can be provided over the sensor. As shown in FIG. 8, for example, the sensor/tissue interface layer 36 may include three sublayers 36a, 36b, and 36c. The sublayer 36a, a layer which promotes tissue ingrowth, preferably is made from a biocompatible material that permits the penetration of capillaries 37 into it, even as fibrotic cells 39 (scar tissue) accumulate on it. Gore-Tex® Vascular Graft material (ePTFE), Dacron® (PET) Vascular Graft materials which have been in use for many years, and MEDPOR Biomaterial produced from high-density polyethylene (available from POREX Surgical Inc.) are examples of materials whose basic composition, pore size, and pore architecture promote tissue and vascular ingrowth into the tissue ingrowth layer.

The sublayer 36b, on the other hand, preferably is a biocompatible layer with a pore size (less than 5 micrometers) that is significantly smaller than the pore size of the tissue ingrowth sublayer 36a so as to prevent tissue ingrowth. A presently preferred material from which the sublayer 36b is to be made is the Preclude Periocardial Membrane (formerly called GORE-TEX Surgical Membrane), available from W.L. Gore, Inc., which consists of expanded polytetra-fluoroethylene (ePTFE).

The third sublayer 36c acts as a molecular sieve, i.e., it provides a molecular weight cut-off function, excluding molecules such as immunoglobulins, proteins, and glycoproteins while allowing the analyte or analytes of interest to pass through it to the indicator molecules (either coated directly on the sensor body 12 or immobilized within a matrix layer 14).

Many well known cellulose-type membranes, e.g., of the sort used in kidney dialysis filtration cartridges, may be used for the molecular weight cut-off layer 36c.

As will be recognized, the sensor as shown in FIG. 6 is wholly self-contained such that no electrical leads extend into or out of the sensor body, either to supply power to the sensor (e.g., for driving the source 18) or to transmit signals from the sensor. All of the electronics illustrated in FIG. 2 may be housed in a module 66 as shown in FIG. 6.

As also will be recognized, the fluorescence-based sensor embodiments described in FIGS. 6-8 are just examples to which the disclosed invention may be applied. The present invention may also be applied in a number of other applications such as, for example, an absorbance-based sensor or a refractive-index-based sensor as described in U.S. patent application Ser. No. 09/383,148, filed Aug. 28, 1999, incorporated herein by reference.

The invention having been thus described, it will be apparent to those skilled in the art that the same may be varied in many ways without departing from the spirit and scope of the invention. For example, while the invention has been described with reference to an implanted sensor device, the principles of the invention may be applied to any printed circuit board that has wireless communication functions using an on-board data or signal power transfer function. Any and all such modifications are intended to be encompassed by the following claims.

What is claimed is:

1. A printed circuit device, comprising:
    a substrate including a circuit component section and a coil section that is separate from the circuit component section, said substrate being formed substantially of ferrite material, said substrate having top and bottom surfaces, first and second side surfaces between said top and bottom surfaces along a major dimension thereof, and first and second end surfaces between said top and bottom surfaces along a minor dimension thereof;
    at least one circuit component mounted to a main surface of said substrate in said circuit component section; and
    a conductor formed around said coil section of said substrate and extending over one of said main surfaces and side surfaces in a coil pattern; and
    wherein said printed circuit device is a component of an implantable sensor device that is capable of performing quantitative analyte measurements within a body of a living organism.

2. The printed circuit device of claim 1, wherein said at least one circuit component lead is routed through a via formed in said substrate.

3. The printed circuit device of claim 2, wherein said at least one circuit component comprises a light-emitting diode (LED) and a lead for said LED.

4. The printed circuit device of claim 3, wherein said lead for said LED is a drive lead.

5. The printed circuit device of claim 2, wherein said at least one circuit component lead is routed through a plurality of vias formed in said substrate.

6. The printed circuit device of claim 5, wherein a plurality of circuit component leads are routed through a plurality of vias formed in said substrate.

7. The printed circuit device of claim 1, wherein said coil is edge-joined around said substrate.

8. The printed circuit device of claim 1, wherein said coil is used for transfer of data signals to an external device.

9. The printed circuit device of claim 1, wherein said coil is used for inductive transfer of electric power from an external power supply.

10. The printed circuit device of claim 1, wherein said at least one circuit component comprises a light-emitting diode (LED) and wherein said printed circuit device further including at least one photodetector.

11. The printed circuit device of claim 1, further comprising a via formed in said substrate for routing of a conductor for a circuit component.

12. The printed circuit device of claim 1, wherein the conductor is printed on the substrate.

13. In an electronic device having an integrated circuit formed on a printed circuit device and an inductive coil for data and/or power transfer, the improvement comprising:
    forming a substrate of said printed circuit device substantially of ferrite material such that said substrate includes a coil section and a separate circuit component section; and
    forming the inductive coil around said coil section of said substrate of the printed circuit device and using said printed circuit device as a ferrite core for said inductive coil; and
    wherein said printed circuit device is a component of an implantable sensor device that is capable of performing quantitative analyte measurements within a body of a living organism.

14. A fluorescence sensor device, comprising:
    a light source for introducing light into a fluorescent indicator that interacts with a medium;
    a photodetector for detecting light emitted by said fluorescent indicator in response to the introduced light, and for outputting a signal proportional to the detected light, the response of the fluorescent indicator varying in accordance with the presence and quantity of an analyte in the medium;
    a coil for receiving electrical power from an external power supply, and for communicating said signal to an external processing device; and
    a substrate including a circuit component section and a coil section that is separate from the circuit component section, said substrate being formed substantially of ferrite material, said light source and said photodetector being mounted to said circuit component section of said substrate, and said coil being formed around said coil section of said substrate such that said ferrite material increases induction characteristics of said coil.

15. The fluorescence sensor device of claim 14, wherein said coil extends around opposing surfaces of said substrate.

16. The fluorescence sensor device of claim 14, wherein said light source comprises a component that is routed through a via formed in said substrate.

17. The fluorescence sensor device of claim 14, wherein said coil is edge-wrapped around said substrate.

18. The fluorescence sensor device of claim 14, wherein said coil is used for communication of data signals to an external device.

19. The fluorescence sensor device of claim 14, wherein said coil is used for inductive reception of electric power from an external power supply.

20. The fluorescence sensor device of claim 14, wherein said device comprises an implantable sensor device that performs quantitative analyte measurements within a body of a living organism.

21. The fluorescence sensor device of claim 14, wherein said device comprises an implantable sensor device that performs qualitative analyte measurements within a body of a living organism.

22. The fluorescence sensor device of claim 20, wherein said light source comprises a light-emitting diode (LED) and said substrate further including at least one photodetector.

23. The fluorescence sensor device of claim 14, further comprising a via formed in said substrate for routing of a conductor for a circuit component.

* * * * *